United States Patent [19]

Cevasco et al.

[11] Patent Number: 5,118,809
[45] Date of Patent: Jun. 2, 1992

[54] PROCESS FOR THE PREPARATION OF SUBSTITUTED AND UNSUBSTITUTED-2,3-PYRIDINEDICARBOXYLATES FROM CHLOROMALEATE OR CHLOROFUMARATE OR MIXTURES THEREOF

[75] Inventors: Albert A. Cevasco, Somerset; George A. Chiarello, Mercer; William F. Rieker, Middlesex, all of N.J.

[73] Assignee: American Cyanamid Company, Stamford, Conn.

[21] Appl. No.: 538,861

[22] Filed: Jun. 15, 1990

[51] Int. Cl.$^5$ ............................................. C07D 213/69
[52] U.S. Cl. ................................... 546/250; 546/321
[58] Field of Search ............................. 546/250, 321

[56] References Cited

U.S. PATENT DOCUMENTS

| | | | |
|---|---|---|---|
| 4,723,011 | 2/1988 | Doehner, Jr. | 546/250 |
| 4,758,667 | 7/1988 | Szczeparski et al. | 546/278 |
| 4,798,619 | 1/1989 | Los | 546/5 |
| 4,871,859 | 10/1989 | Gupton et al. | 546/250 |
| 4,948,896 | 8/1990 | Nagao | 546/250 |
| 5,008,392 | 4/1991 | Meier et al. | |

FOREIGN PATENT DOCUMENTS

| | | | |
|---|---|---|---|
| 0299362 | 1/1989 | European Pat. Off. | 546/300 |
| 2174395 | 5/1986 | United Kingdom. | |

OTHER PUBLICATIONS

Chemical Abstracts, vol. 105, No. 23, Abstract 208,767z, p. 584, Dec. 8, 1986.

*Primary Examiner*—C. Warren Ivy
*Assistant Examiner*—Barbara Twardzik
*Attorney, Agent, or Firm*—Alice C. Brennan

[57] ABSTRACT

There is provided a process for the preparation of dialkyl pyridinedicarboxylate compounds and derivatives thereof by reacting a dialkyl chloromaleate or chlorofumarate or a mixture thereof with an ammonium salt optionally in the presence of ammonia and an appropiately substituted $\alpha,\beta$-unsaturated aldehyde or ketone.

16 Claims, No Drawings

PROCESS FOR THE PREPARATION OF SUBSTITUTED AND UNSUBSTITUTED-2,3-PYRIDINEDICARBOXYLATES FROM CHLOROMALEATE OR CHLOROFUMARATE OR MIXTURES THEREOF

BACKGROUND OF THE INVENTION

Pyridine-2,3-dicarboxylates are useful intermediates in the preparation of highly effective herbicidal 2-(2-imidazolin-2-yl)nicotinic acids, esters and salts. Said herbicidal agents and methods for their preparation are disclosed in U.S. Pat. Nos. 4,798,619 and 4,758,667. Imidazolinyl nicotinates and derivatives thereof are highly effective herbicides at low rates of application and demonstrate selective control of noxious weeds in the presence of important agronomic crops while exhibiting exceptionally low mammalian toxicity.

Processes for the preparation of substituted pyridine-2,3-dicarboxylates are described in U.S. Pat. Nos. 4,723,011, 4,871,859 and European Patent Application Publication Number 0 299 362-A1 among others, however, there is still a need in the art for yet more suitable methods of preparation of these important intermediates.

It is an object of this invention to provide a method for the preparation of substituted and unsubstituted-2,3-pyridinedicarboxylates utilizing dialkyl chloromaleate or dialkyl chlorofumarate or a mixture thereof, an ammonium salt, optionally in the presence of ammonia and an appropriately substituted α,β-unsaturated aldehyde or ketone.

SUMMARY OF THE INVENTION

The invention herein described relates to a novel method for the preparation of substituted and unsubstituted 2,3-pyridinecarboxylates of formula I

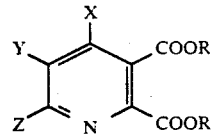

wherein R is $C_1$–$C_6$ alkyl; X and Z are independently hydrogen, halogen, $C_1$–$C_4$ alkyl, $C_1$–$C_4$ alkoxy or $C_2$–$C_5$ alkenyl and Y is hydrogen, halogen, $C_1$–$C_6$ alkyl optionally substituted with one to three halogens, hydroxy groups, $C_1$–$C_4$ alkoxy groups or $C_1$–$C_4$ alkylthio groups, $C_1$–$C_4$ alkoxycarbonyl, aminocarbonyl, phenyl, substituted phenyl, phenoxy, substituted phenoxy, phenylthio or substituted phenylthio. Compounds of formula I are useful as intermediates in the preparation of herbicidal 2-(2-imidazolin-2-yl)nicotinates. Among the methods of preparation of said herbicidal nicotinates is that described in U.S. Pat. No. 4,758,667 and illustrated below.

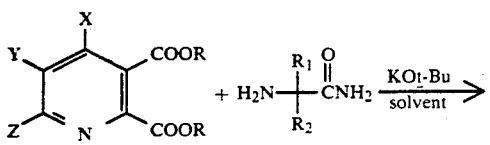

-continued

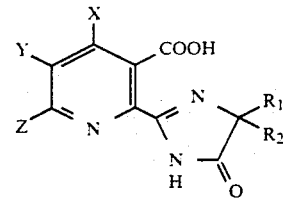

wherein $R_1$ is hydrogen or $C_1$–$C_4$ alkyl; $R_2$ is hydrogen, halogen, $C_1$–$C_4$ alkyl, $C_3$–$C_6$ cycloalkyl or $R_1$ and $R_2$ may be taken together to form a $C_3$–$C_6$ cycloalkyl optionally substituted with methyl and X, Y and Z are as described for formula I.

DETAILED DESCRIPTION OF THE INVENTION

It has now been found that pyridine-2,3-dicarboxylates of formula I can be prepared efficiently and effectively from chloromaleates of formula II or chlorofumarates of formula III or mixtures thereof wherein R is $C_1$–$C_6$ alkyl by reacting the chloromaleate or chlorofumarate with at least one molar equivalent of an ammonium salt such as ammonium acetate, optionally in the presence of ammonia, in a suitable solvent such as a $C_1$–$C_4$ alkylalcohol to form an enamine intermediate and reacting said intermediate with at least one molar equivalent of an α,β-unsaturated aldehyde or ketone of formula IV wherein X, Y and Z are as described for formula I in the presence of an acid such as acetic acid. The process is shown in flow diagram I.

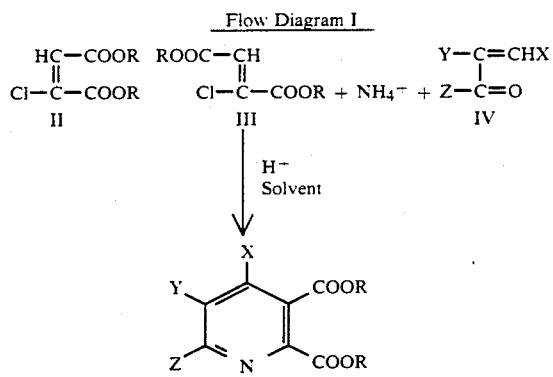

Ammonium salts which may be used in the process of the invention include ammonium acetate, ammonium propionate, ammonium sulfate, ammonium carbonate, ammonium bicarbonate, ammonium carbamate, ammonium sulfamate and the like.

In one embodiment of the invention, a polar solvent may be utilized such as an alcohol, nitrile such as acetonitrile, a carboxylic acid amide such as N,N-dimethylformamide, N-methylpyrrolidone, a sulfoxide such as dimethylsulfoxide, a sulfone and the like.

Among the α,β-unsaturated aldehydes or ketones of formula IV which may be used in the process of the invention are acrolein, methacrolein, ethacrolein, crotonaldehyde, methyl vinyl ketone, α-n-butylacrolein, 4-methyl-2-hexanal, α-methoxymethacrolein, α-chloromethacrolein, α-trifluoromethacrolein, cinnamaldehyde, α-ethoxyacrolein, methyl α-formylacrylate, α-(2-cyanoethyl)acrolein and the like.

In a further embodiment of the invention, the reaction mixture comprising the above-formed intermediate and the α,β-unsaturated aldehyde or ketone of formula IV may be treated with a dehydrogenation catalyst such as that which is conventional in the art including metals or compounds of platinum, palladium, ruthenium, iridium, nickel, iron, copper, antimony, cobalt, rhodium and the like. The dehydrogenation catalyst is commonly used in the form of the dehydrogenation metal or compound thereof deposited on a suitable support such as alumina, carbon, clay, zeolite, chromia, zirconia and the like.

Thus, pyridine-2,3-dicarboxylates containing substituents in the 4,5 and 6 positions may be conveniently prepared by admixing a formula II dialkyl chloromaleate or a formula III dialkyl chlorofumarate with at least one molar equivalent of an ammonium salt optionally in the presence of anhydrous ammonia in a suitable solvent, optionally heating said mixture until reaction is essentially complete, optionally filtering said reaction mixture and adding to the filtrate or to the unfiltered reaction mixture an acid such as a mineral acid, sulfuric acid, phosporic acid, an organic acid such as formic acid, acetic acid or propionic acid and the like to obtain a pH of at least about 4 and at least one molar equivalent of an α,β-unsaturated aldehyde or ketone of formula IV optionally in the presence of a dehydrogenation catalyst, optionally heating the resulting reaction mixture until formation of the desired formula I pyridinedicarboxylate is complete. The reaction product can be isolated using standard purification techniques such as fractional distillation, recrystallization, extraction, liquid chromatography and the like.

The rate of formation of the enamine intermediate and the formula I pyridinedicarboxylate is temperature dependent, thus, reaction time can be effectively diminished by heating the reaction mixtures at temperatures of about 45° C. or greater.

In order to facilitate a further understanding of the invention, the following examples are presented primarily for the purpose of illustrating certain more specific details thereof and the invention is not to be deemed limited thereby. The terms $^1$HNMR and IR designate proton nuclear magnetic resonance and infrared respectively. Unless otherwise noted, all parts are parts by weight.

EXAMPLE 1

Preparation of diethyl
5-ethyl-2,3-pyridinedicarboxylate from diethyl chloromaleate in the presence of ammonia and ammonium acetate A mixture of diethyl chloromaleate (4.10 g, 0.02 mol) and ammonium acetate (1.54 g, 0.02 mol) in ethanol is treated with anhydrous ammonia (1.0 g, 0.06 mol), stirred at room temperature 16 hours, treated with 10 mL of acetic acid and 2-ethacrolein (5.04 g, 0.06 mol) in two portions over a total of 16 hours at 70° C. and concentrated in vacuo to afford an oil residue. The residue is taken up in toluene, filtered and the filtrate is evaporated to dryness in vacuo to afford an oil. The resultant oil is vacuum distilled to afford the title product as a tan oil, bp 151°–152° C./2 mm Hg.

EXAMPLE 2

Preparation of diethyl
5-ethyl-2,3-pyridinedicarboxylate from diethyl chloromaleate in the presence of ammonium acetate A mixture of a total of 4.62 g (0.06 mol) of ammonium acetate and diethyl chloromaleate (4.10 g, 0.02 mol) in ethanol is heated at 70° C. for a total of 48 hours, filtered and the filter cake is washed with ethanol. The combined filtrates are treated with 10 mL acetic acid and 2-ethacrolein (4.62 g, 0.06 mol) in two portions, heated at 70° C. for a total of 6 hours and concentrated in vacuo to give an oil residue. The thus-obtained oil is vacuum distilled to afford the title product as a tan oil, bp 151°–152° C./2 mm Hg.

EXAMPLE 3

Preparation of diethyl
5-ethyl-2,3-pyridinedicarboxylate from diethyl chlorofumarate A stirred mixture of ammonium acetate (7.0 g, 0.09 mol), anhydrous ammonia (0.2 g, 0.012 mol) and a 7:1 mixture of diethyl chlorofumarate and diethyl chloromaleate in ethanol is heated at 70° C. for 12 hours, cooled to 25° C. and filtered. The filter cake is washed with ethanol and the combined filtrates are concentrated in vacuo. The thus-obtained concentrated reaction mixture is treated with acetic acid and 2-ethacrolein (5.0 g, 0.06 mol), heated at 70° C. with stirring for 6 hours and concentrated in vacuo to give an oil residue. The resultant residue is taken up in methylene chloride, washed with water and fractionally distilled to obtain the title product as a tan oil, bp 151°–152° C./2 mm Hg.

EXAMPLE 4

Preparation of dialkyl
substituted-2,3-pyridinedicarboxylate from dialkyl chloromaleate Using essentially the same procedure described in Example 1 and substituting the appropriate α,β-unsaturated aldehyde, the following compounds are obtained and identified by $^1$HNMR and IR spectral analysis.

| X | Y | Z | R |
|---|---|---|---|
| H | CH$_3$ | H | C$_2$H$_5$ |
| H | CH$_2$OCH$_3$ | H | C$_2$H$_5$ |
| H | CH$_2$Cl | H | C$_2$H$_5$ |
| H | H | H | C$_2$H$_5$ |

EXAMPLE 5

Preparation of dialkyl
substituted-2,3-pyridinedicarboxylate from dialkyl chlorofumarate Using essentially the same procedure described in Example 3 and substituting the appropriate α,β-unsaturated aldehyde gives the following compounds

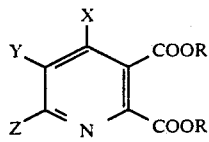

| X | Y | Z | R |
|---|---|---|---|
| H | CH₃ | H | C₂H₅ |
| H | CH₂OCH₃ | H | C₂H₅ |
| H | CH₂Cl | H | C₂H₅ |
| H | H | H | C₂H₅ |

The above compounds are identified by $^1$HNMR and IR spectral analysis.

What is claimed is:

1. A process for the preparation of a compound of formula I

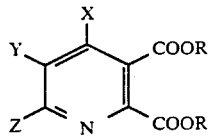

wherein R is $C_1$–$C_6$ alkyl; X and Z are independently hydrogen, halogen, $C_1$–$C_4$ alkyl, $C_1$–$C_4$ alkoxy or $C_2$–$C_5$ alkenyl and Y is hydrogen, halogen, $C_1$–$C_6$ alkyl optionally substituted with one to three halogens, hydroxy groups, $C_1$–$C_4$ alkoxy groups or $C_1$–$C_4$ alkylthio groups, $C_1$–$C_4$ alkoxycarbonyl, aminocarbonyl, phenylthio or phenoxy, phenyl which comprises reacting a compound of formula II or formula III or a mixture thereof

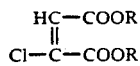

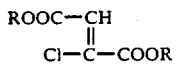

wherein R is $C_1$–$C_6$ alkyl with an ammonium salt in the presence of a solvent, optionally in the presence of ammonia, to form an intermediate, reacting said intermediate with an α,β-unsaturated aldehyde or ketone of formula IV

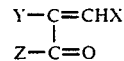

wherein X, Y and Z are as described above in the presence of an acid to form the formula I pyridinedicarboxylate compound.

2. The process according to claim 1 for the preparation of the pyridinedicarboxylate compound of formula I wherein X and Z are hydrogen and Y is hydrogen, halogen or $C_1$–$C_4$ alkyl optionally substituted with one to three halogens, $C_1$–$C_4$ alkoxy groups or $C_1$–$C_4$ alkylthio groups.

3. The process according to claim 1 wherein the solvent is a polar solvent and the acid is acetic acid.

4. The process according to claim 1 wherein the intermediate is formed at a temperature of about 45° C. or greater.

5. The process according to claim 1 wherein the formula I pyridinedicarboxylate compound is formed at a temperature of about 45° C. or greater.

6. The process according to claim 1 wherein the α,β-unsaturated aldehyde or ketone of formula IV is present in the amount of at least one molar equivalent.

7. The process according to claim 2 wherein the formula I compound prepared is dialkyl pyridine-2,3-dicarboxylate.

8. The process according to claim 2 wherein the formula I compound prepared is dialkyl 5-methyl-2,3-pyridinedicarboxylate.

9. The process according to claim 2 wherein the formula I compound prepared is dialkyl 5-ethyl-2,3-pyridinedicarboxylate.

10. The process according to claim 2 wherein the formula I compound prepared is dialkyl 5-(methoxymethyl)-2,3-pyridinedicarboxylate.

11. The process according to claim 2 wherein the formula I compound prepared is dialkyl 5-(chloromethyl)-2,3-pyridinedicarboxylate.

12. The process according to claim 7 wherein the formula I compound is diethyl pyridine-2,3-dicarboxylate.

13. The process according to claim 8 wherein the formula I compound prepared is diethyl 5-methyl-2,3-pyridinedicarboxylate.

14. The process according to claim 9 wherein the formula I compound prepared is diethyl-5-ethyl-2,3-pyridinedicarboxylate.

15. The process according to claim 10 wherein the formula I compound prepared is diethyl 5-(methoxymethyl)-2,3-pyridinedicarboxylate.

16. The process according to claim 11 wherein the formula I compound prepared is diethyl 5-(chloromethyl)-2,3-pyridinedicarboxylate.

* * * * *